United States Patent [19]

Casey et al.

[11] Patent Number: 4,965,201
[45] Date of Patent: Oct. 23, 1990

[54] PREPARATION OF DICARBOXYLIC ACID

[76] Inventors: John Casey, Stanwick; Roy T. Dobb, Odell; Roger Jeffcoat, Stanwick, all of Great Britain

[21] Appl. No.: 350,378

[22] Filed: May 11, 1989

[30] Foreign Application Priority Data

May 11, 1988 [EP] European Pat. Off. ........ 88200957.4

[51] Int. Cl.$^5$ ............................ C12P 7/64; C12P 7/42; C12R 1/72
[52] U.S. Cl. .................................. 435/134; 435/142; 435/255; 435/921
[58] Field of Search ................ 435/134, 142, 255, 921

[56] References Cited

U.S. PATENT DOCUMENTS

| | | | |
|---|---|---|---|
| 3,843,466 | 10/1974 | Akabori et al. ...................... | 435/142 |
| 3,912,586 | 10/1975 | Kaneyuki et al. .................... | 435/142 |
| 3,975,234 | 8/1976 | Hitzman .............................. | 435/142 |
| 4,339,536 | 7/1982 | Kato et al. .......................... | 435/142 |
| 4,474,882 | 10/1984 | Kunishige et al. ................... | 435/142 |
| 4,564,594 | 1/1986 | Goldberg et al. .................... | 435/142 |

OTHER PUBLICATIONS

Chemical Abstracts, vol. 100, No. 11 (Mar. 1984), p. 432, abstract No. 48258j.
Chemical Abstracts, vol. 98, No. 9 (Feb. 1983), p. 337, abstract No. 68659a.
Chemical Abstracts, vol. 94, No. 9 (Mar. 1981), p. 570, abstract No. 63753j.

*Primary Examiner*—Herbert J. Lilling
*Attorney, Agent, or Firm*—Cushman, Darby & Cushman

[57] ABSTRACT

The invention provides a process for preparing medium chain dicarboxylic acids by biochemical oxidation so that in particular $C_8$ and $C_{10}$ dicarboxylic acids are prepared from nontoxic levels of $C_8$–$C_{14}$ fatty acids using a nitrogen-restricted yeast propagated in a carbon substrate containing growth medium. Preferably the fatty material is supplied to the yeast in the form of a glyceride. Also it is preferred that the amount of nitrogen in the biomass is between 4 and 9%, in particular between 5.5 and 7% (w/w).

9 Claims, No Drawings

PREPARATION OF DICARBOXYLIC ACID

The invention relates to a process for the preparation of dicarboxylic acid by biochemical oxidation of monocarboxylic acid. More in particular this biochemical oxidation is carried out by propagating a yeast in a suitable substrate.

The biochemical preparation of medium chain dicarboxylic acids from various starting materials is a well-known process and has been disclosed inter alia in: JP-A-49019085 (Asahi Electrochem Ind KK) in which an ester of a monocarboxylic acid containing more than 8 carbon atoms is oxidized to dicarboxylic acid by culturing Candida tropicalis in a medium also containing urea, phosphates, and several metal salts. JP-A-48039690 (Mitsui Shipbuilding Eng.) in which n.paraffins of 8-13 C atoms are oxidized to dicarboxylic acids by Candida lopstra MF 1 in a medium containing ammonium nitrate, phosphate, metal salts and yeast extract.

JP-A-74043156 (Fujimsawa Pharm Co Ltd) in which n.hexadecane was oxidized to adipic acid by Candida trooicalis in a medium also containing ammonium phosphate, biotin, several potassium phosphates and magnesium sulphate.

JP-A-58121797 (Mitsui Petrochem Ind KK) in which n.paraffins are oxidized to dicarboxylic acids by a Torulopsis yeast strain whilst supplying a nitrogen source and phosphate continuously or intermittently. The ammonium ion concentration in the culture medium is e.g. 100-700 ppm, preferably 100-400 ppm. The technique of supplying nitrogen and phosphate continuously or intermittently is said to remarkably increase the final concentration of dicarboxylic acid. US-A-3 975 234 (Phillips Petroleum Co) in which C6-C22 n.alkanes, n.alkylalcohols or mixtures thereof are oxidized to dicarboxylic acid by a mutant strain of Torulopsis bombicola which has been previously grown on a hydrocarbon-free growth medium containing at least one carbohydrate source and a very low percentage of metabolisable nitrogen, leading to a maximum of 3% nitrogen in the yeast and subsequently contacting this microorganism under non-growth conditions in a non-growth converting medium with the n.alkane; n.alkylalcohol or mixture thereof, which medium is free of a nitrogen source but contains a carbohydrate. This two-step process led to a more selective conversion of the n.alkane n.alkyl alcohol or mixture thereof into the corresponding dicarboxylic acid and consequently less degradation in the carbon chain than had been obtained so far.

It is object of the present invention to provide a process for the biochemical oxidation of medium chain monocarboxylic acids so as to obtain selectively and in good yield dicarboxylic acids in a relatively simple one-step process.

According to the present invention $C_8$, $C_{10}$ and $C_{12}$ dicarboxylic acids (depending on the conditions) are prepared by propagating a nitrogen-restricted yeast in a carbon source-containing medium containing non-toxic levels of $C_8$-$C_{18}$ monocarboxylic acids or glycerides. Under a nitrogen-restricted yeast is to be understood a yeast which contains a sub-optimal amount of metabolisable nitrogen, preferably an amount between 4 and 9% by weight, better still above 5.5 but below 7% (w.w.). Nitrogen is preferably supplied to the medium in judicious amounts of preferably $NH_4^+$-ions and/or organic nitrogen.

The carbon source in the medium can be e.g. glucose, sucrose, glycerol or ethanol in suitable amounts such as 30 g sucrose per litre medium containing 3.5 g of ammoniumphosphate $(NH_4)_2 HPO_4$.

The lipid substrate for bioconversion is supplied to the medium as the growth phase nears completion. The The $C_8$-$C_{18}$ monocarboxylic acids can be supplied to the medium as such, but then care has to be taken that the concentration in the medium is kept below 0.2 g/litre for $C_8$-$C_{10}$ mono carboxylic acids as to avoid toxicity effects on the yeast. Often therefore it is deemed advantageous to supply the monocarboxylic acid in the form of an ester, preferably as a triglyceride, where the toxicity problem hardly applies.

The yeast employed in the practice of this invention can be a Candida or Torulopsis. Particularly preferred are Candida species such as C. cloaceae especially strains or mutants thereof which exhibit low beta oxidation activity. One particular strain viz. Candida cloacae 5 GLA 12 has the surprising property of producing predominantly $C_8$, $C_{10}$ and C 12 dicarboxylic acid (depending on the conditions) from the fatty acids in natural oils.

The details of the deposited organisms are as follows:

| Organism | Reference | Accession No. |
| --- | --- | --- |
|  | 5GLA12 | NCIMB 40128 |
| candida | 5GLB19 | NCIMB 40129 |
| cloacae | 5GLB21 | NCIMB 40130 |

The microorganisms are deposited with the material collection of Industrial and marine Bacteria, whose address is P.O. Box 31, 135 Abbey Road, Aberdeen, AB9 8DB, Scotland under the terms of the Budapest Treaty.

The time of the biochemical oxidation to dicarboxylic acid is generally from 20 to 200 hours. The temperature for the oxidation usually is in the range from 15 to about 45° C., preferably between 20 and 37° C.

Good results are obtained by including in the medium apart from the judicial amount of nitrogen compound, metal salts, especially magnesium and calcium, phosphates and organic co-factors like biotin, thiamin, nicotinic acid, pyrodoxin and pantothenate.

After the biochemical oxidation has taken place the microorganism is separated from the growth medium by standard techniques and the dicarboxylic acid recovered e.g. by solvent extraction and further purified. The dicarboxylic acids so obtained are useful ingredients in the manufacture of e.g. polyamides and polyesters.

EXAMPLES 1-4

Organisms and incubation conditions

A strain of Candida cloacae (FERM P-410) known to be able to utilize alkanes, fatty acids and triglycerides as sole carbon source was used as the parent strain in a mutation programme to generate mutants blocked in β-oxidation. Mutagenesis was achieved by use of N-methyl-N-nitrosoguanidine and β-oxidation negative mutants isolated by selecting for poor growth on yeast nitrogen base (Difco) with a carbon source of fatty acid or alkane but good growth on yeast nitrogen base with acetate or glucose as carbon source.

Mutants were grown in a defined medium consisting of a carbon source of glucose added at appropriate levels and a nitrogen source of $(NH_4)_2 HPO_4$ or yeast extract (Difco) added at appropriate levels. Other components of the medium were:

| Component | Amount |
|---|---|
| $Na_2SO_4$ | 0.75 g/l |
| $KH_2PO_4$ | 3.2 g/l |
| $MgCl_2$ | 1.0 g/l |
| $ZnSO_4$ | 10 mg/l |
| $MnSO_4$ | 10 mg/l |
| $FeSO_4$ | 10 mg/l |
| Nicotinic acid | 15 mg/l |
| Pantothenate | 3 mg/l |
| Pyridoxine | 10 mg/l |
| Thiamine | 4 mg/l |
| Biotin | 50 ug/l |

The resulting yeast cells from the various propagations were of a range of nitrogen contents and this was calculated using the formula:

$$\frac{N \text{ used}}{\text{biomass}} \times 100 = \% N \text{ in biomass}$$

At stationary phase (24–48h) triglyceride substrate (a synthetic triglyceride containing 70% C8 and 30% C10 fatty acids) was added and incubation continued. Samples were removed for analysis of product formation which was carried out by acidification followed by extraction with ether and analysis of dicarboxylic acids as their silyl ethers by gas-liquid chromatography.

Five batches of C.cloacae (mutant 5GLB19) were propagated in media where the carbon source was glucose, 25 g/l and the nitrogen source was $(NH_4)_2 HPO_4$ at concentrations ranging from 1 to 4 g/l. Synthetic triglyceride, 25 g/l, was added at stationary phase and incubation continued for 4 days. Products were C8 and C10 dicarboxylic acids and C8 and C10 fatty acids (Table 1).

TABLE 1

| $(NH_4)_2 HPO_4$ g/l | % N in biomass | dicarboxylic acid (C8 + C10) g/l | fatty acid (C8 + C10) g/l |
|---|---|---|---|
| 1.5 | 3.6 | 1.01 | 0 |
| 2.5 | 5.5 | 2.0 | 0.05 |
| 3.5 | 7.6 | 1.21 | 0.95 |
| 4 | 8.8 | 0.5 | 1.6 |

In this example, yeast cells with a nitrogen content of 5.5% w/w produced the greatest amount of dicarboxylic acid. Free fatty acids were also produced, chiefly by the nitrogen-rich cells. Variable amounts of C6 dicarboxylic acid (adipic acid) were also observed reflecting some remaining β-oxidation activity.

The quantities of adipic acid are not included in these results.

EXAMPLES 5-12

Nine batches of C.cloacae (mutant 5GLB21) were propagated in media where the carbon source was sucrose, 30 g/l and the nitrogen source was $(NH_4)_2 HPO_4$ at concentrations ranging from 2.5-5.5 g/l. Synthetic triglyceride (30 g/l) was added at stationary phase and incubation continued for 5 days. Products were C8 and C10 dicarboxylic acids and C8 and C10 fatty acids (Table 2).

TABLE 2

| $(NH_4)_2 HPO_4$ g/l | % N in biomass | dicarboxylic acid (C8 + C10) g/l | fatty acid (C8 + C10) g/l |
|---|---|---|---|
| 2.0 | 4 | 0.75 | 0.03 |
| 2.5 | 5.3 | 1.23 | 0.05 |
| 3.0 | 5.7 | 3.6 | 0.09 |
| 3.5 | 6.2 | 6.93 | 0.13 |
| 4.0 | 6.7 | 6.15 | 0.1 |
| 4.5 | 7.5 | 1.33 | 2.0 |
| 5.0 | 8.3 | 0.76 | 4.2 |
| 5.5 | 9.0 | 0.31 | 6.2 |

With this mutant, cells with a nitrogen content of 6.2-6.7% w/w produced the greatest levels of dicarboxylic acids. Fatty acids were produced mainly by less nitrogen restricted cells.

EXAMPLES 13-17

Eight batches of C.cloacae (mutant 5GLB21) were propagated in media where the carbon source was sucrose, 30 g/l, and the nitrogen source was yeast extract (Difco) at concentrations ranging from 3-12 g/l.

Synthetic triglyceride (30 g/l) was added at stationary phase and incubation continued for 5 days. Products are shown in Table 3.

TABLE 3

| Yeast extract g/l | % N in biomass | dicarboxylic acid (C8 + C10) g/l | fatty acid (C8 + C10) g/l |
|---|---|---|---|
| 6 | 3.9 | 2.2 | 0.01 |
| 7 | 4.3 | 2.8 | 0.37 |
| 9 | 5.4 | 3.4 | |
| 10 | 5.7 | 4.1 | 0.35 |
| 12 | 6.9 | 3.4 | 0.8 |

EXAMPLES 18-19

C. cloacae (mutant 5GLA12 was propagated in media where the carbon substrate was sucrose, 30 g/l and the nitrogen source was $(NH_4)_2 HPO_4$ at 3 or 3.5 g/l. Coconut oil (42 g/l) was added at stationary phase. Table 4 shows the time course of dicarboxylic acid production by the cells grown with 3.5 g/l $(NH_4)_2 HPO_4$.

TABLE 4

| Reaction time days | Dicarboxylic acid ($C_8 + C_{10}$), g/l |
|---|---|
| 1 | 1.0 |
| 2 | 3.0 |
| 4 | 6.1 |
| 6 | 10.8 |
| 7 | 7.1 |

In this experiment production was maximal by 6 days and declined thereafter. Table 5 shows the maximum total amount of dicarboxylic acids (excluding adipic acid) produced. This was achieved on day 5 or 6 with both batches of yeast.

TABLE 5

| $(NH_4)_2 HPO_4$ g/l | % N in biomass | dicarboxylic acid (C8 + C10) g/l |
|---|---|---|
| 3.0 | 5.5 | 9.9 |
| 3.5 | 7.7 | 10.8 |

Whilst the coconut oil substrate contained a range of fatty acids from C8-C18, strain 5GLA12 had the ability to selectively accumulate dicarboxylic acids of the chain length C8 and C10 Table 6 compares the chain lengths of the dicarboxylic products of Example 19 (6 day incubation) with the chain lengths of the fatty acids in the coconut oil substrate and shows that $C_8$ and $C_{10}$ dicarboxylic acids are selectively produced.

TABLE 6

| Chain length | Coconut oil fatty acids (% composition) | Dicarboxylic acids (% composition) |
|---|---|---|
| C6 | 0 | 6 |
| C8 | 7 | 59 |
| C10 | 9 | 35 |
| C12 | 50 | |
| C14 | 17 | |
| C16 | 10 | |
| C18:1 | 7 | |

EXAMPLES 20-24

Mutant 5LGA12 was propagated in a medium of the same composition as in Table 1 except that the concentrations of all the components were doubled. The carbon source was sucrose 60 g/l and the nitrogen source was $(NH_4)_2 HPO_4$ at concentrations ranging from 5-10 g/l. A growth period of 48h was allowed to ensure complete utilization of sucrose and then the coconut oil substrate was added at 42 g/l.

Table 7 shows that the increased biomass generated by this more concentrated medium allowed a faster rate and a greater concentration of dicarboxylic acid accumulation than in Table 4. The dicarboxylic acid product was predominantly C8 plus C10 with some C12 in the earlier samples. In this experiment biomass containing 5.8% nitrogen produced the most dicarboxylic acid product. The amount and yield of C8 plus C10 dicarboxylic acid, especially at the optimum nitrogen content in the biomass could not have been produced solely from the C8 plus C10 fatty acids in the coconut oil. The bulk of the dicarboxylic acid product must have been generated by chain shortening of the longer chain fatty acids.

EXAMPLE 25

Mutant 5G LA 12 was grown in a Chemap fermenter in a medium of the same composition as in Table 1. except that it was double strength. The carbon source was sucrose at 60 g/l. This experiment was carried out at a 2 l scale using an aeration rate of 0.5 vvm and an impeller speed of 600 rpm during the growth phase. After a growth period of 1.5 days the biomass had reached 24 g/l and then 50 ml/l of coconut oil was added and the impeller speed increased to 1500 rpm. Further additions of oil were made over the course of the experiment. Daily samples were removed from the fermenter and the products analysed. Table 8. shows the amount and type of dicarboxylic acids produced. There are two clear differences when the process is carried out in a stirred tank fermenter as opposed to shake flasks. Firstly the nature of the products accumulated was different, there being large amounts of C12 dicarboxylic acid, and secondly the overall rate of dicarboxylic acid production was double that in shake flasks.

EXAMPLES 26-30

Batches of mutant 5G LA 12 were propagated in shake flasks on double strength growth medium using sucrose at 60 g/l. At the end of the growth phase 50 g/l quantities of lipid substrate were added. These substrates were: coconut oil, sodium tallowate (70% C16, 30% C18), olive, hexadecane, pentadecane. After 6 days the products were analysed and results are shown in Table 9.

It was clear that, in all but one case, regardless of the nature of the lipid substrate, the dicarboyxlic acids accumulated were of chain length C8, C10, C12, although the proportions may be influenced by the nature of the substrate. The exception was with the pentadecane where the products were C7, C9, C11.

TABLE 7

| $(NH_4)_2 HPO_4$ g/l | % N in biomass | Incubation time, d | Dicarboxylic acids | | | | Total (C8-C12) | Residual triglyceride (g/l) | Product Yield (%) |
|---|---|---|---|---|---|---|---|---|---|
| | | | C6 | C8 | C10 | C12 | | | |
| 5 | 4.3 | 6 | 0.2 | 0.3 | 0.12 | 0.12 | 0.54 | 30 | 4 |
| 5.5 | 4.7 | 3 | 0 | 1.6 | 2.6 | 2.6 | 6.8 | 23 | 34 |
| | | 5 | 0.38 | 4.8 | 5.2 | 0.6 | 10.6 | 18 | 43 |
| | | 6 | 0.55 | 6.2 | 2.8 | 0.7 | 9.7 | 8 | 28 |
| 6 | 5.7 | 3 | 0 | 1.5 | 1.6 | 1.9 | 5.0 | 28 | 34 |
| | | 4 | 0.17 | 1.8 | 2.1 | 2.2 | 6.1 | 18 | 25 |
| | | 5 | 0.33 | 4.2 | 5.3 | 2.3 | 11.8 | 14 | 41 |
| | | 6 | 0.28 | 4.3 | 4.1 | 0.3 | 8.7 | 10 | 27 |
| 7 | 5.8 | 3 | 0 | 1.6 | 2.0 | 2.8 | 6.4 | 21 | 30 |
| | | 5 | 0.56 | 6.0 | 5.3 | 0.9 | 12.2 | 11 | 39 |
| | | 6 | 0.37 | 3.9 | 2.1 | 0.1 | 6.1 | 1 | 19 |
| 10 | 8.1 | 3 | 0.24 | 2.4 | 2.5 | 1.1 | 6.0 | 10 | 18 |
| | | 5 | 1.3 | 8.1 | 2.7 | 0 | 10.8 | 0.7 | 26 |
| | | 6 | 0.7 | 5.0 | 0.6 | 0.02 | 5.6 | 0 | 15 |

TABLE 8

| Incubation Product time h. | Dicarboxylic acids, g/l | | | Total | yield (%) |
|---|---|---|---|---|---|
| | C8 | C10 | C12 | | |
| 20 | 0.4 | 0.9 | 2.2 | 3.5 | |
| 44 | 2.3 | 3.8 | 6.0 | 12.1 | |
| 70 | 3.1 | 5.5 | 8.4 | 17.0 | 27 |
| 95 | 4.8 | 7.4 | 11.9 | 24.1 | 32 |
| 117 | 5.5 | 8.1 | 13.3 | 26.9 | 29 |
| 142 | 6.7 | 8.9 | 12.2 | 27.8 | |

TABLE 9

| Lipid substrate | Dicarboxylic acids, g/l | | | Total |
|---|---|---|---|---|
| | C8 | C10 | C12 | |
| Coconut oil | 11.5 | 12.7 | 2.8 | 27.0 |
| Sodium tallowate | 2.2 | 1.3 | 2.1 | 5.6 |
| Olive oil | 3.9 | 8.7 | 8.4 | 21.0 |
| Hexadecane | 8.5 | 8.8 | 0.9 | 18.2 |
| | C7 | C9 | C11 | |
| Pentadecane | 0.1 | 19.8 | 6.3 | 26.2 |

We claim:
1. A process for preparing medium chain dicarboxylic acids by biochemical oxidation characterized in that $C_8$ to $C_{12}$ dicarboxylic acids are prepared from non-toxic levels of $C_8$–$C_{18}$ fatty acids or esters thereof using a nitrogen-restricted yeast propagated in a carbon substrate containing growth medium wherein the amount of nitrogen present is between 4 and 9% (w/w).

2. A process according to claim 1 in that the amount of nitrogen is between 5.5 and 7% (w/w).

3. A process according to claim 1 in which the nitrogen in the yeast cells is supplied as $NH_4^+$ ions and/or organic nitrogen.

4. A process according to claim 1, characterized in that the concentration of the carbon substrate is between 10 and 100 g/l.

5. A process according to claim 1 characterized in that the medium also contains metal salts and organic cofactors.

6. A process according to claim 1 characterized in that the biochemical oxidation is carried out at a temperature between 15 and 45° and for a reaction period between 20 and 200 hours.

7. A process according to claim 1 characterized in that the yeast is a Candida species.

8. A process according to claim 7 characterized in that the Candida species is *Candida cloaceae*.

9. A process according to claim 1, wherein the ester is a glyceride.

* * * * *